United States Patent
Kaneko et al.

(10) Patent No.: US 11,073,525 B2
(45) Date of Patent: Jul. 27, 2021

(54) AUTOMATIC ANALYZER

(71) Applicant: HITACHI HIGH-TECHNOLOGIES CORPORATION, Tokyo (JP)

(72) Inventors: Yasuo Kaneko, Tokyo (JP); Takayuki Noda, Tokyo (JP); Toshihide Hanawa, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 390 days.

(21) Appl. No.: 16/076,718

(22) PCT Filed: Jan. 20, 2017

(86) PCT No.: PCT/JP2017/001982
§ 371 (c)(1),
(2) Date: Aug. 9, 2018

(87) PCT Pub. No.: WO2017/145601
PCT Pub. Date: Aug. 31, 2017

(65) Prior Publication Data
US 2019/0079107 A1 Mar. 14, 2019

(30) Foreign Application Priority Data
Feb. 25, 2016 (JP) .............................. JP2016-033859

(51) Int. Cl.
*G01N 35/00* (2006.01)
*G01N 35/10* (2006.01)
*G16H 10/40* (2018.01)

(52) U.S. Cl.
CPC ....... *G01N 35/00663* (2013.01); *G01N 35/00* (2013.01); *G01N 35/00722* (2013.01);
(Continued)

(58) Field of Classification Search
None
See application file for complete search history.

(56) References Cited

U.S. PATENT DOCUMENTS 5,695,718 A * 12/1997 Imai ................. G01N 35/00594
340/521
5,730,939 A  3/1998 Kurumada et al.
(Continued)

FOREIGN PATENT DOCUMENTS

JP  08-262031 A  10/1996
JP  2012-113354 A  6/2012

OTHER PUBLICATIONS

International Search Report of PCT/JP2017/001982 dated Apr. 11, 2017.
(Continued)

*Primary Examiner* — Kathryn Wright
(74) *Attorney, Agent, or Firm* — Mattingly & Malur, PC (57) ABSTRACT

The automatic analyzer includes: a device state managing unit that manages a device state of the automatic analyzer; an abnormality detecting unit that detects abnormality of the automatic analyzer based on information of the device state managed by the device state managing unit and a predetermined reference; an alarm planning unit that plans at least two alarms including an abnormality occurrence alarm and an handling available alarm regarding each of abnormality items detected by the abnormality detecting unit, the abnormality occurrence alarm being planned for notification to a user in a case where the abnormality occurs, and the handling available alarm being planned for notification to the user in a case where the automatic analyzer is in a device state where the automatic analyzer is available for handling the abnormality; and a notifying unit that notifies the alarms planned by the alarm planning unit.

9 Claims, 7 Drawing Sheets

(52) U.S. Cl.
CPC ... *G01N 35/00871* (2013.01); *G01N 35/1002* (2013.01); *G16H 10/40* (2018.01); *G01N 2035/009* (2013.01); *G01N 2035/00673* (2013.01); *G01N 2035/00742* (2013.01); *G01N 2035/00891* (2013.01)

(56) References Cited

U.S. PATENT DOCUMENTS

| | | | | |
|---|---|---|---|---|
| 2007/0233303 A1* | 10/2007 | Naito | ............ | G06F 19/00 700/108 |
| 2011/0077871 A1* | 3/2011 | Fukuma | ............ | G01N 35/00871 702/21 |
| 2014/0250339 A1* | 9/2014 | Ishii | ............ | G01N 35/00623 714/57 |

OTHER PUBLICATIONS

International Preliminary Report on Patentability received in corresponding International Application No. PCT/JP2017/001982 dated Sep. 7, 2018.

* cited by examiner

| TARGET | ABNORMALITY | ABNORMALITY OCCURRENCE TIME / DISPLAY OPERATION INSTRUCTION | HANDLING AVAILABLE TIME / TIMING | ACTION |
|---|---|---|---|---|
| SAMPLE | CLOGGING<br>DEFICIENCY<br>SERUM INFORMATION ABNORMALITY (SUCH AS HEMOLYSIS)<br>MEASUREMENT RESULT ABNORMALITY | SAMPLE MASKING<br>SAMPLE COLLECTION<br>SAMPLE SUPPLY STOP | SAMPLE COLLECTION END<br>MEASUREMENT END | SAMPLE ADJUSTMENT (FOR EXAMPLE, CENTRIFUGAL SEPARATION)<br>SAMPLE REPLENISHMENT<br>REMEASUREMENT<br>ADDITIONAL ITEM MEASUREMENT |
| REAGENT | DEFICIENCY (MANUALLY REGISTRATION/DISPOSAL) | ANALYZING UNIT MASKING | ANALYZING UNIT MASKING END | SAMPLE REGISTRATION/DISPOSAL<br>ANALYZING UNIT MASKING RELEASING |
| | DEFICIENCY (AUTOMATICALLY REGISTRATION/DISPOSAL) | REAGENT REGISTRATION | REAGENT DISTRIBUTION END | SAMPLE REGISTRATION/DISPOSAL |
| | MEASUREMENT RESULT ABNORMALITY | REAGENT MASKING CALIBRATION | MEASUREMENT END | SAMPLE EXAMINATION REMEASUREMENT |
| DEVICE | STOP LEVEL ABNORMALITY | MAINTENANCE | | |
| | SAMPLE SUPPLY STOP LEVEL ABNORMALITY (THE SAMPLE SUPPLY CANNOT RESTART) | — | MEASUREMENT END | MAINTENANCE |
| | SAMPLE SUPPLY STOP LEVEL ABNORMALITY (THE SAMPLE SUPPLY CAN RESTART) | ANALYZING UNIT MASKING | ANALYZING UNIT MASKING END | MAINTENANCE (CORRESPONDING ANALYZING UNIT) ANALYZING UNIT MASKING RELEASING |
| | NEGLIGIBLE LEVEL ABNORMALITY | — | MEASUREMENT END | MAINTENANCE |
| ABNORMALITY ALREADY KNOWN TO USER DURING OPERATION (ALARM WHICH IS NORMAL TO USER AND IS NOT NECESSARY TO BE NOTIFIED) | | *SET ALARM NOT TO BE NOTIFIED | *SET ALARM NOT TO BE NOTIFIED | *SET ALARM NOT TO BE NOTIFIED |

ALARM NOTIFICATION DESTINATION USER SETTING SCREEN

USER REGISTRATION :

902

| USER ID | NAME | MAIN RESPONSIBLE DEVICE | SKILL LEVEL | WORKING HOUR |
|---------|------|-------------------------|-------------|---------------|
| 001 | HITACHI TARO | DEVICE A | LEVEL 3 | 08:00~17:00 |
| 002 | SATO HIROSHI | DEVICE A | LEVEL 1 | 08:00~17:00 |
| 003 | OZAWA HANAKO | DEVICE C | LEVEL 2 | 17:00~08:00 |
| 004 | AIKAWA ICHIRO | DEVICE B | LEVEL 3 | 17:00~08:00 |
| 005 | KOIZUMI MACHIKO | DEVICE C | LEVEL 1 | 12:00~17:00 |

903 — ALARM NOTIFICATION DESTINATION USER :
● RESPONSIBLE USER FOR DEVICE    ○ USER POSITIONED NEAR DEVICE    ○ USER HAVING HANDLING SKILL    ○ ALL USERS

904 — ALARM HANDLING WAIT TIMEOUT: 15 MINUTES

905 — NOTIFICATION OF TIMEOUT : ● RENOTIFICATION TO SAME USER    ○ NOTIFICATION TO ALL USERS

SET

AUTOMATIC ANALYZER

TECHNICAL FIELD

The present invention relates to an automatic analyzer that performs qualitative and quantitative analysis of biological samples such as blood and urine.

BACKGROUND ART

In an automatic analyzer that performs qualitative and quantitative analysis of a specific component included in a biological sample (hereinafter, simply referred to as "sample") such as blood or urine by using the sample and a reagent, in order to prevent a delay of reporting of a measurement result to clinical sites, abnormality during the operation is notified to a user to urge the user to handle with the abnormality rapidly by displaying a message on a screen or using an alarm function such as a warning sound or a warning lamp. In particular, recently, along with the sophistication of medical treatments and an increase in the number of pre-treatment examinations, the importance of a rapid examination and rapid examination result reporting has increased, and a reduction in down time caused by the occurrence of abnormality and improvement of the examination efficiency have been required.

As a background art relating to a process of the abnormality occurrence time, for example, PTL 1 (JP-A-8-262031) discloses an automatic analyzer that can analyze an analytic item in a sample by measuring a reaction solution obtained by mixing the sample and a reagent. This automatic analyzer detects abnormality of the sample and the reagent and displays a list in which the detected abnormality is associated with the analytic item.

CITATION LIST

Patent Literature

PTL 1: JP-A-8-262031

SUMMARY OF INVENTION

Technical Problem

However, the operation of an automatic analyzer varies depending on individual laboratories in many cases.

Accordingly, in a case where the operation contents regarding the determination or reporting of abnormality do not match with conditions set in an automatic analyzer, the contents of an alarm generated by the automatic analyzer do not match with the operation in a laboratory, which may lead to deterioration in examination efficiency or a delay of examination result reporting.

The present invention has been made in consideration of the above-described circumstances, and an object thereof is to provide an automatic analyzer that can prevent deterioration in examination efficiency and a delay of examination result reporting.

Solution to Problem

In order to achieve the object, according to the present invention, there is provided an automatic analyzer that performs analysis using a sample and a reagent, the automatic analyzer including: a device state managing unit that manages a device state of the automatic analyzer; an abnormality detecting unit that detects abnormality of the automatic analyzer based on information of the device state managed by the device state managing unit and a predetermined reference; an alarm planning unit that plans at least two alarms including an abnormality occurrence alarm and an handling available alarm regarding each of abnormality items detected by the abnormality detecting unit, the abnormality occurrence alarm being planned for notification to a user in a case where the abnormality occurs, and the handling available alarm being planned for notification to the user in a case where the automatic analyzer is in a device state where the automatic analyzer is available for handling the abnormality; and a notifying unit that notifies the alarms planned by the alarm planning unit.

Advantageous Effects of Invention

According to the present invention, deterioration in examination efficiency or a delay of examination result reporting can be prevented.

DESCRIPTION OF EMBODIMENTS

An embodiment of the present invention will be described with reference to the drawings.

Figure 1:
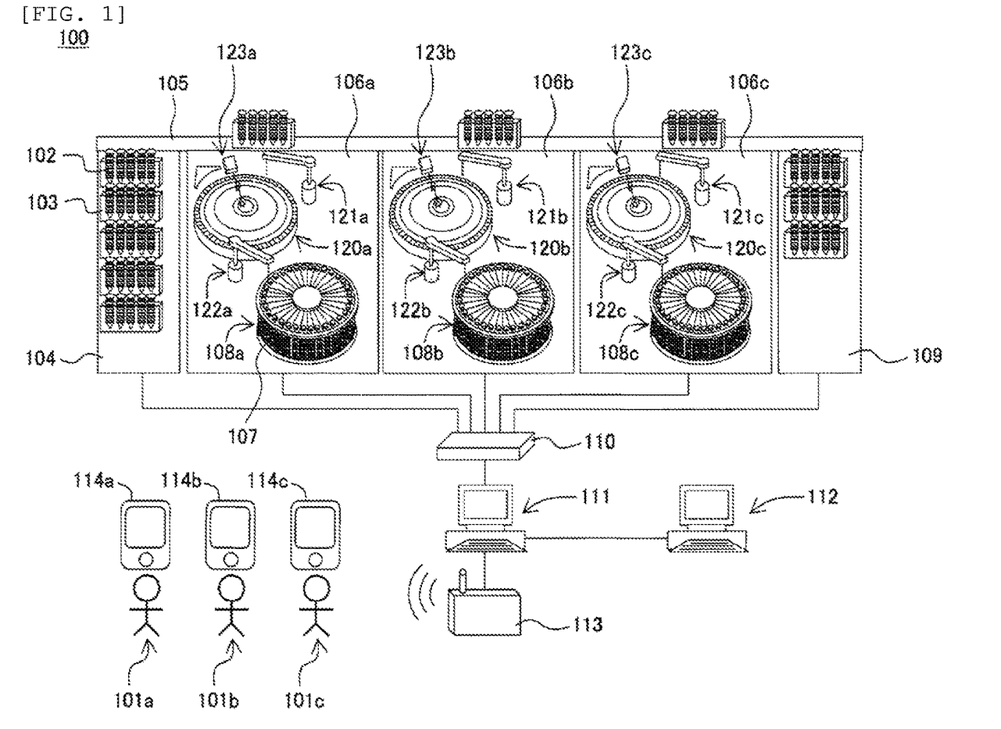
FIG. 1 is a diagram schematically illustrating an overall configuration of an automatic analyzer according to an embodiment of the present invention.

FIG. 1 is a diagram schematically illustrating an overall configuration of an automatic analyzer according to the embodiment.

In FIG. 1, roughly, the automatic analyzer 100 includes a sample loading unit 104, analyzing units 106a, 106b, and 106c, a sample housing unit 109, a transportation line 105, an operating unit PC 111, and remote operation terminals 114a, 114b, and 114c.

A sample as an analysis target is housed in a sample container 102, plural sample containers 102 are loaded on a sample rack 103, and the sample rack 103 is loaded in the sample loading unit 104. This sample loading unit 104 is connected to the sample housing unit 109 that houses the sample rack 103 through the transportation line 105 through which the sample rack 103 is transported. One or more (for example, in the embodiment, three) analyzing units 106a, 106b, and 106c are disposed along the transportation line 105.

The operating unit PC 111 controls an overall operation of the automatic analyzer 100 and is connected to respective configurations of the automatic analyzer 100 through a communication device 110 (for example, a hub). In addition, the operating unit PC 111 is connected to a wireless device 113 (for example, a wireless router) and is wirelessly connected to one or more (for example, in the embodiment, three) remote operation terminals 114a, 114b, and 114c so as to communication with them. In addition, the operating unit PC 111 is also connected to a higher-level host system 112 that controls an overall operation of an analysis system including the automatic analyzer 100.

A sample as an analysis target is housed in a sample container 102, plural sample containers 102 are loaded on a sample rack 103, and the sample rack 103 is loaded in the sample loading unit 104. This sample loading unit 104 is transported to each of the analyzing units 106a, 106b, and 106c, the sample housing unit 109, or the like through the transportation line 105. Examples of the sample housed in the sample container 102 include a calibration sample used for calibration measurement, a precision control sample used for precision control measurement, and a patient sample that is a biological sample such as blood or urine. In each of the sample containers 102 loaded on the sample rack 103, a tag 102a (for example, a barcode or a RFID) for identifying the sample to be housed is provided. Identification information is read by a reading device (not illustrated) and transmitted to the operating unit PC 111 or the like.

For example, the analyzing unit 106a includes: a reaction disk 120a that includes plural reaction containers; a sample dispensing mechanism 121a that dispenses the sample housed in the sample container 102 into the reaction container, the sample container 102 being transported through the transportation line 105; a reagent disk 108a on which plural reagent containers 107 each of which houses a reagent used for analyzing the sample are loaded; a reagent dispensing mechanism 122a that dispenses the reagent of the reagent container 107 into the reaction container; and a photometric mechanism 123a that measures an absorbance, a scattered light intensity, or the like of a mixed solution (reaction solution) of the sample and the reagent housed in the reaction container. For example, the analyzing units 106b and 106c have the same configuration as the analyzing unit 106a, and include reaction disks 120b and 120c, sample dispensing mechanisms 121b and 121c, reagent disks 108b and 108c, reagent dispensing mechanisms 122b and 122c, and photometric mechanisms 123b and 123c, respectively.

In the automatic analyzer 100, plural (for example, three) remote operation terminals 114a, 114b, and 114c are associated with one or more (for example, three) users 101a, 101b, and 101c relating to the operation of the automatic analyzer 100, and are connected to the operating unit PC 111 through the wireless device 113 so as to communicate with them, respectively. Accordingly, the users 101a, 101b, and 101c carry the remote operation terminals 114a, 114b, and 114c associated with them such that information can be exchanged between the specific users 101a, 101b, and 101c and the operating unit PC 111.

Figure 2:
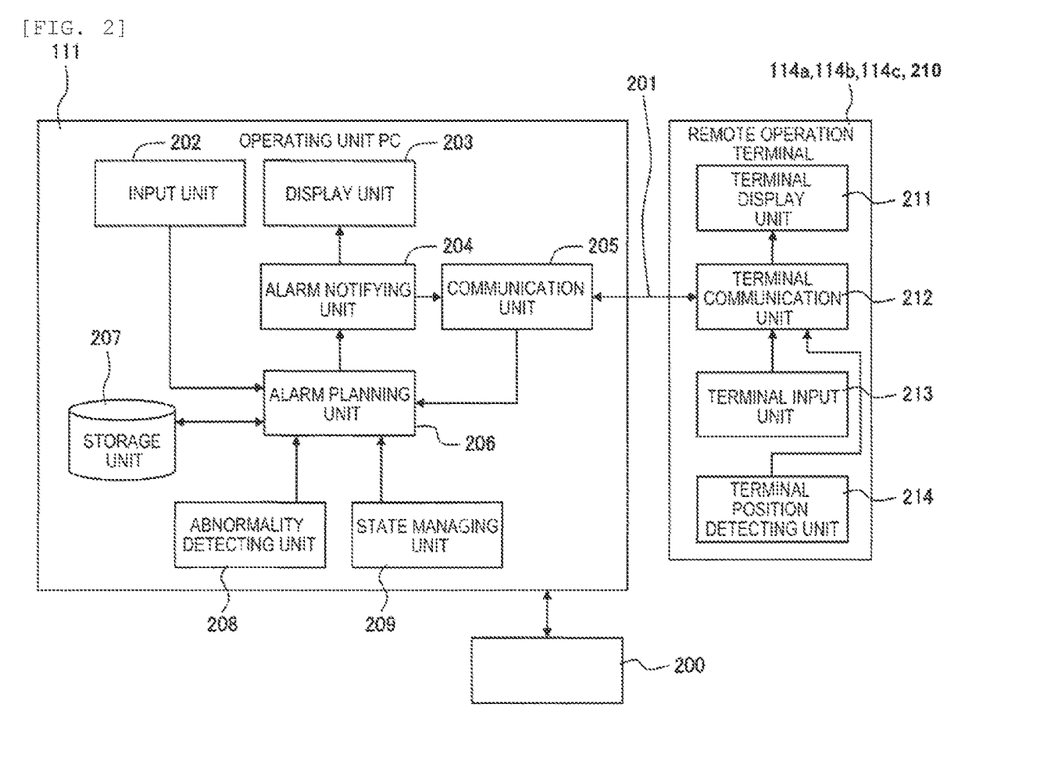
FIG. 2 is a functional block diagram illustrating an operating unit PC and remote operation terminals.

FIG. 2 is a functional block diagram illustrating the operating unit PC and the remote operation terminals.

FIG. 2 illustrates a case where information exchanges between the operating unit PC 111 and the remote operation terminals 114a, 114b, and 114c by communication 201 through the wireless device 113.

In FIG. 2, for example, the operating unit PC 111 includes an input unit 202, a display unit 203, an alarm notifying unit 204, a communication unit 205, an alarm planning unit 206, a storage unit 207, an abnormality detecting unit 208, and a state managing unit 209. The operating unit PC communicates with another configuration 200 (for example, the sample loading unit 104, the analyzing unit 106a, 106b, or 106c, the sample housing unit 109, or the transportation line 105) of the automatic analyzer 100.

The input unit 202 is, for example, a keyboard or a mouse and performs, for example, the pressing (mouse-clicking) of buttons on various operation screens (described below) displayed on the display unit 203 using a mouse cursor or the input of numbers or characters into an input frame using a keyboard. That is, the input unit 202 and the display unit 203 configure a GUI (Graphical User Interface).

The state managing unit 209 determines and manages a current state (device state) of each of the configurations of the automatic analyzer 100 based on information of events occurring on the automatic analyzer 100. As the device state, various states of the automatic analyzer 100 can be considered, and examples thereof include a normal state, clogging of the dispenser, a decrease in the remaining amount of the sample, the reagent, or a cleaning solution, and a sample position.

The abnormality detecting unit 208 detects abnormality of the automatic analyzer 100 based on information, the device state, and the like obtained from detectors (not illustrated) provided in the automatic analyzer 100, and a predetermined reference (for example, a detection theory of abnormality).

The alarm planning unit 206 plans various alarms regarding each of abnormality items detected by the abnormality detecting unit 208 based on a setting of an alarm notification setting screen 301 described below. The kinds of alarms planned by the alarm planning unit 206 include at least two alarms including an abnormality occurrence alarm (first alarm type) and a handling available alarm (second alarm type), the abnormality occurrence alarm is planned for notification in a case where abnormality occurs, and the handling available alarm is planned for notification in a case where whether or not the automatic analyzer 100 is available for handling the abnormality based on information from the state managing unit 209 (in other words, whether or not the automatic analyzer transitions into a device state where a process of improving the abnormality is executable) and it is determined that the automatic analyzer is in a device state where the automatic analyzer is available for handling the abnormality.

In the storage unit 207, the contents of the alarms planned by the alarm planning unit 206, setting information relating to the notification of the alarms (information such as whether or not each of the alarms is notified per each of the abnormality items, a notification destination, the device state where the automatic analyzer is available for handling the abnormality, and a timing of the device state), and the like are stored.

The notifying unit (alarm notifying unit) 204 notifies the alarms planned by the alarm planning unit 206 to the users 101a, 101b, and 101c. Specifically, the notifying unit 204 the alarms to the users 101a, 101b, and 101c by displaying a screen for notifying the occurrence of abnormality at the center of the display unit 203 or a terminal display unit 211 (described below), by generating a warning sound from a specific device including a remote operation terminal 210 (described below), or by turning on and off an alarm lamp (not illustrated).

In addition, in FIG. 2, for example, each of the remote operation terminals 114a, 114b, and 114c includes a terminal display unit 211, a terminal communication unit 212, a terminal input unit 213, and a terminal position detecting unit 214. Each of the remote operation terminals 114a, 114b, and 114c communicates with the operating unit PC 111 through the wireless device 113 so as to obtain information from the other configuration 200 (for example, the sample loading unit 104, the analyzing unit 106a, 106b, or 106c, the sample housing unit 109, or the transportation line 105) of the automatic analyzer 100 or to perform the operation of the other configuration 200.

In the remote operation terminal 210, as in the case of the operating unit PC 201, a GUI is configured by the terminal display unit 211 and the terminal input unit 213 such that various kinds of information (including information of the alarms) transmitted from the operating unit PC 201 is received and displayed on the terminal display unit 211 or an operation instruction or the like is input to the automatic analyzer 100 through the terminal input unit 213 and is transmitted to the operating unit PC 201.

The terminal position detecting unit 214 detects a positional relationship (referred to as "position information") relative to the automatic analyzer 100 and the remote operation terminal 210, specifically, a direction or a distance of the remote operation terminal 210 when seen from a specific configuration of the automatic analyzer 100, and transmits the detected position information to the operating unit PC 111 through the terminal communication unit 212. Examples of a method of detecting the position information include a method of detecting the position information of the remote operation terminal using a GPS (Global Position System) to perform calculation using the preset position information of the automatic analyzer 100 and a method of detecting the relative position or the distance based on a communication field intensity.

In a large-scale laboratory or the like, an operation in which plural automatic analyzers are used by plural users may be considered. In this case, this operation can be handled by configuring a system or a network to secure various communication states such as a case where a relationship is established between one automatic analyzer and plural users (remote operation terminals), a case where a relationship is established between plural automatic analyzers and one user, or a case where a relationship is established between plural automatic analyzers and plural users In addition, in the embodiment, a case where a portable remote operation terminal and the automatic analyzer wirelessly communicate with each other will be described as an example. However, a system in which the communication can be performed by wire or using a fixed terminal according to the operation state of the automatic analyzer can also be configured.

Figure 3:
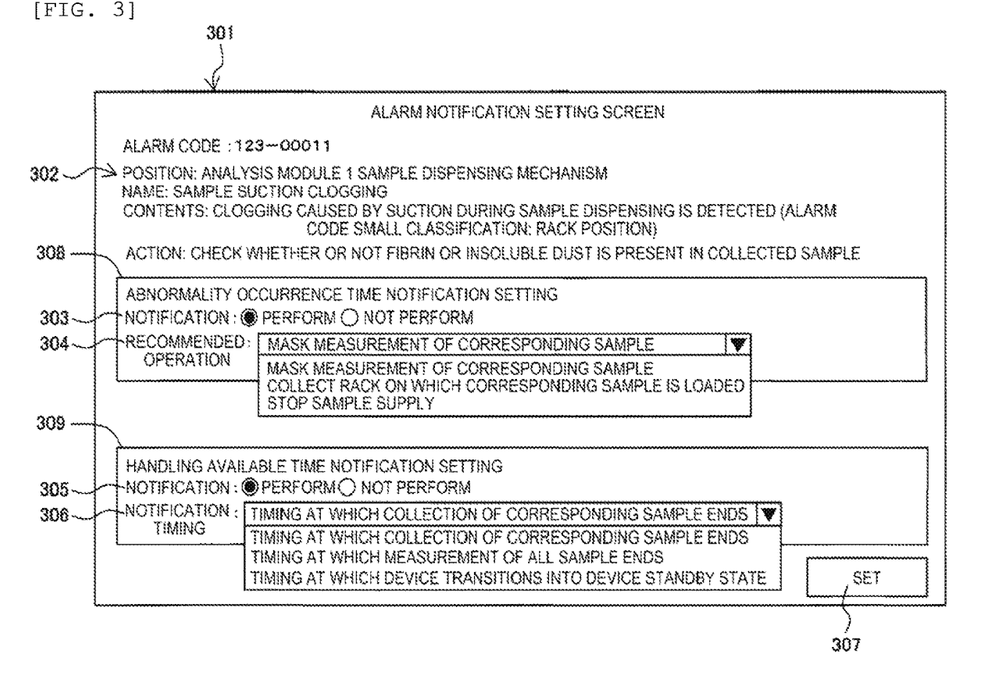
FIG. 3 is a diagram illustrating an alarm notification setting screen.

FIG. 3 is a diagram illustrating an alarm notification setting screen.

The alarm notification setting screen 301 illustrated in FIG. 3 is displayed on the display unit 203 of the operating unit PC 111 or the terminal display unit 211 of the remote operation terminal 114a, 114b, or 114c, relates each of various alarms pre-registered for each of abnormalities that may occur in the automatic analyzer 100, and is a screen for performing setting regarding whether or not to notify the alarm of the abnormality occurrence time, whether or not to notify the alarm of the handling available time, and a handling available timing. Regarding the operation of the alarm notification setting screen 301, for example, there may be a case where a setting regarding the alarm notification is preset before using the automatic analyzer 100 or a case where a setting regarding the alarm notification is set when abnormality occurs and alarm notification is performed.

In FIG. 3, for example, the alarm notification setting screen 301 includes an alarm content display unit 302, an abnormality occurrence time notification setting unit 308, a handling available time notification setting unit 309, and a set button 307.

On the alarm content display unit 302, the contents of an alarm for the abnormality that may occur in the automatic analyzer 100 are displayed and, for example, include an alarm code, a position, a name, contents, and an action.

The abnormality occurrence time notification setting unit 308 sets a notification setting of the alarm of the abnormality occurrence time, and includes: a notification setting unit 303 that immediately sets whether or not to notify the alarm of the abnormality occurrence time; and a recommended operation setting unit 304 that selectively sets a recommended device operation among predetermined plural candidates (candidates of device operations), the recommended device operation being displayed to the user when the abnormality occurs and the alarm is notified. In the example of FIG. 3, an alarm relating to clogging during sample suction is used as an example. In the recommended operation setting unit 304, the recommended operation is selected among an operation of masking the measurement of the corresponding measurement, an operation of collecting a sample rack on which the corresponding sample is loaded, and an operation stopping the supply of the sample. This way, the action of the abnormality occurrence time can be smoothly handled by the user presetting a recommended device operation according to the operation based on the urgency of the measurement of the sample and the influence of clogging on the device.

The handling available time notification setting unit 309 sets a notification setting of the alarm that is generated when the user can handle the abnormality after the occurrence of the abnormality, and includes: a notification setting unit 305 that sets whether or not to notify the alarm when the user can handle the abnormality target; and a notification timing setting unit 306 that selects a timing at which the alarm is notified of the handling available time among predetermined plural candidates. In the example of FIG. 3, the notification timing is selected among a timing at which the collection of the sample ends, a timing at which the measurement of all the samples ends, and a timing at which the automatic analyzer 100 transitions into a device standby state. This way, a mismatch between the contents of the alarm that is generated by the automatic analyzer and the operation in a laboratory can be prevented by setting a timing at which the automatic analyzer enters a state where the user can handle the abnormality target as a default timing and setting an optimum handling timing for the circumstances of the user (operation side). Therefore, deterioration in examination efficiency or a delay of examination result reporting can be prevented.

The set button 307 is a button for storing the setting contents input by the alarm notification setting screen 301 in the storage unit 207. In the example illustrated in FIG. 3, the setting regarding whether or not to notify the alarm is shown. However, not only the display of the alarm but also a setting regarding whether or not to activate/inactivate a warning sound or a warning lamp that is generated together with the alarm may be provided so as for the user to perform the setting in more detail.

This way, due to the setting of the alarm notification setting screen 301, whether or not to notify the alarm and an operation of the device that should be performed by the user of the abnormality occurrence time, and whether or not to notify the alarm and the notification timing of the handling available time can be preset. Therefore, the user can recognize abnormality at an appropriate timing, can give a necessary operation instruction to the device, and can take an action timely at a timing at which the device is ready for handling the abnormality. In addition, by presetting an alarm regarding abnormality which is already known to the user during the operation (that is, an alarm regarding abnormality which is normal to the user and is not necessary to be notified) not to be notified, the user is not interrupted by the alarm notification during an examination.

Figure 4:
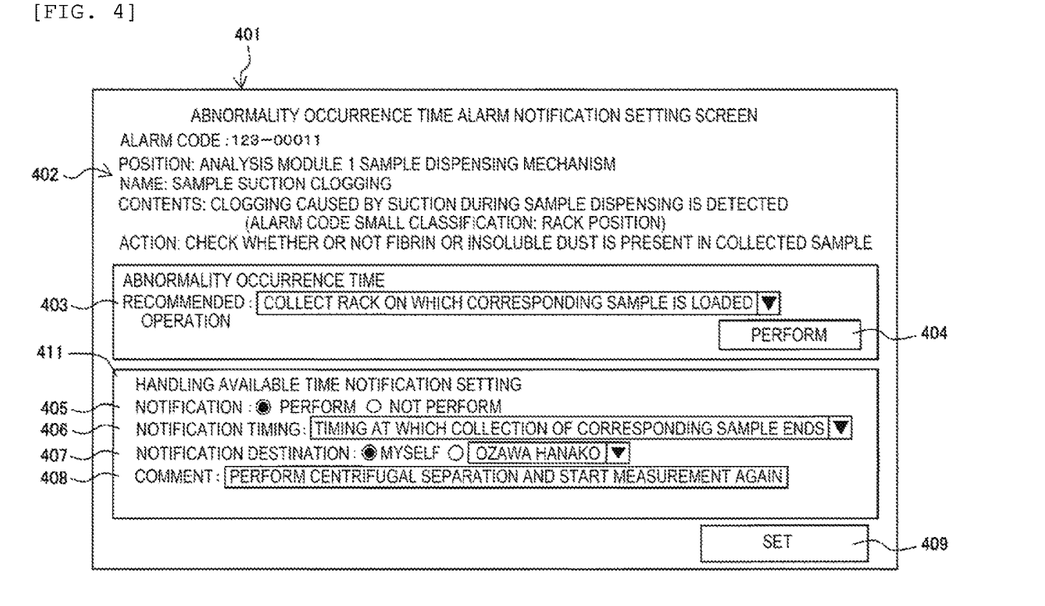
FIG. 4 is a diagram illustrating an abnormality occurrence time alarm notification setting screen.

FIG. 4 is a diagram illustrating an abnormality occurrence time alarm notification setting screen.

An abnormality occurrence time alarm notification setting screen 401 illustrated in FIG. 4 is displayed on the display unit 203 of the operating unit PC 111 or the terminal display unit 211 of the remote operation terminal 114a, 114b, or 114c, and is notified and displayed at a timing at which abnormality occurs according to the setting that is set by the abnormality occurrence time notification setting unit 308 on the alarm notification setting screen 301.

In FIG. 4, for example, the abnormality occurrence time alarm notification setting screen 401 includes an alarm content display unit 402, an abnormality occurrence time recommended operation display unit 403, and a handling available time notification setting unit 411.

On the alarm content display unit 402, for example, an alarm code, a position, a name, contents, and an action are displayed as the contents of the alarm for the abnormality.

The abnormality occurrence time recommended operation display unit 403 displays a recommended operation of the device that should be performed by user in response to the alarm at the abnormality occurrence time, and displays the contents set by the recommended operation setting unit 304 on the alarm notification setting screen 301. The user recognizes the display of the abnormality occurrence time recommended operation display unit 403 and optionally performs the recommended operation by operating a perform button 404. In the abnormality occurrence time recommended operation display unit 403, optionally the recommended operation can be reselected by the user. In this case, the recommended operation can be selectively selected among plural candidates as in the case of the recommended operation setting unit 304 of the alarm notification setting screen 301. In the example of FIG. 4, an operation of collecting the sample and causing the user to check the sample is shown as an action. Therefore, an operation of collecting a rack on which the sample causing the alarm notification is loaded is displayed as the recommended operation of the device.

Figure 7:
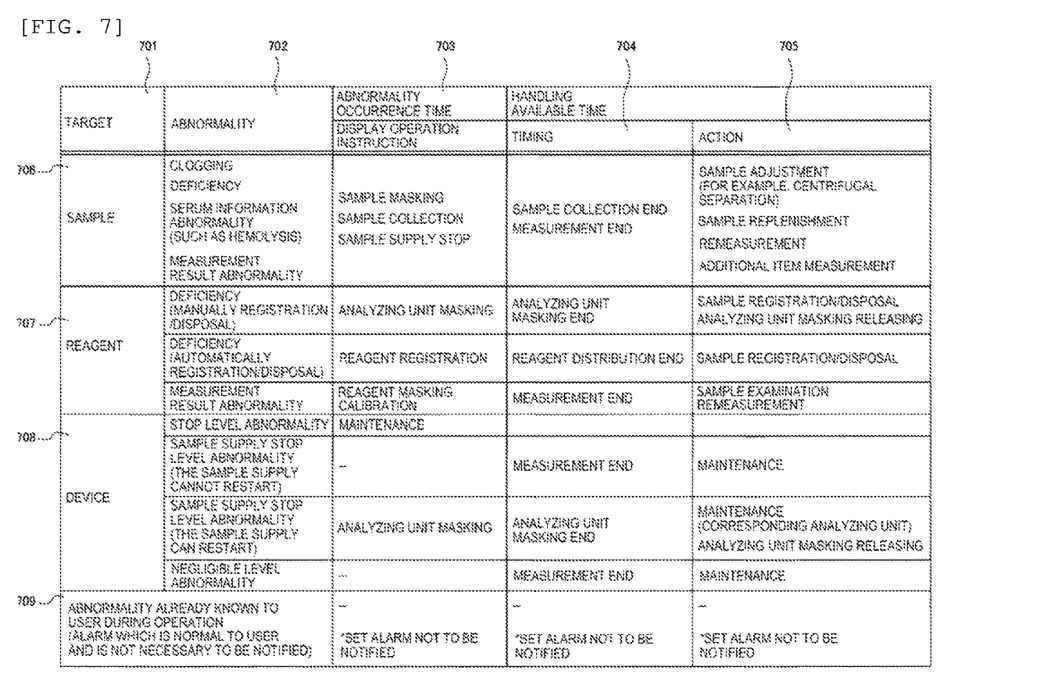
FIG. 7 is a diagram illustrating an example of a correspondence table showing a device operation instruction of the abnormality occurrence time and a timing and an action of the handling available time in the automatic analyzer.

The handling available time notification setting unit 411 sets a notification setting of the alarm that is generated when the user can handle the abnormality after the occurrence of the abnormality, and includes: a notification setting unit 405 that sets whether or not to notify the alarm when the user can handle the abnormality target; a notification timing setting unit 406 that sets a setting of a timing at which the alarm is notified at the handling available time; a notification destination setting unit 407 that sets the user to be notified at the handling available time; and a comment input unit 408 that inputs request contents for the user that takes an action at the handling available time. On the notification setting unit 405 and the notification timing setting unit 406, the contents set by the notification timing setting unit 305 and the notification timing setting unit 306 are displayed. On the notification timing setting unit 406, the contents set by the notification timing setting unit 306 on the alarm notification setting screen 301 are displayed in advance but optionally can be reselected by the user. In this case, the recommended operation can be selectively selected among plural candidates as in the case of the notification timing setting unit 306 of the alarm notification setting screen 301. In the example of FIG. 4, in a case where the collection of the rack as the recommended operation is performed, the user can check the user after the collection of the sample (rack). Therefore, "the timing at which the collection of the sample ends" is displayed on the display unit as the notification timing of the alarm. That is, in the notification timing setting unit 406, the notification timing at which the fact that the automatic analyzer is in a device state, in which the user can handle the abnormality in a case where the recommended operation is performed, is notified to the user is displayed on the display unit. For example, the display contents of the recommended operation (corresponding to "device operation instruction") and the display contents of the notification timing are associated with each other in advance as illustrated in FIG. 7 and a relationship therebetween is set in the device.

A set button 409 is a button for storing the setting contents input by the abnormality occurrence time alarm notification setting screen 401 in the storage unit 207.

By setting the abnormality occurrence time alarm notification setting screen 401 as described above, for example, when receiving notification of abnormality, an administrator user can request a responsible user to handle the abnormality of the handling available time by operating the device. In addition, in a case where the user cannot handle the abnormality due to another examination, the administrator user can request another user to handle the abnormality. In addition, in a case where the device is used by plural users, a user that receives notification and instructs an operation of the abnormality occurrence time and a user that takes an action of the handling available time can be separately designated.

Figure 5:
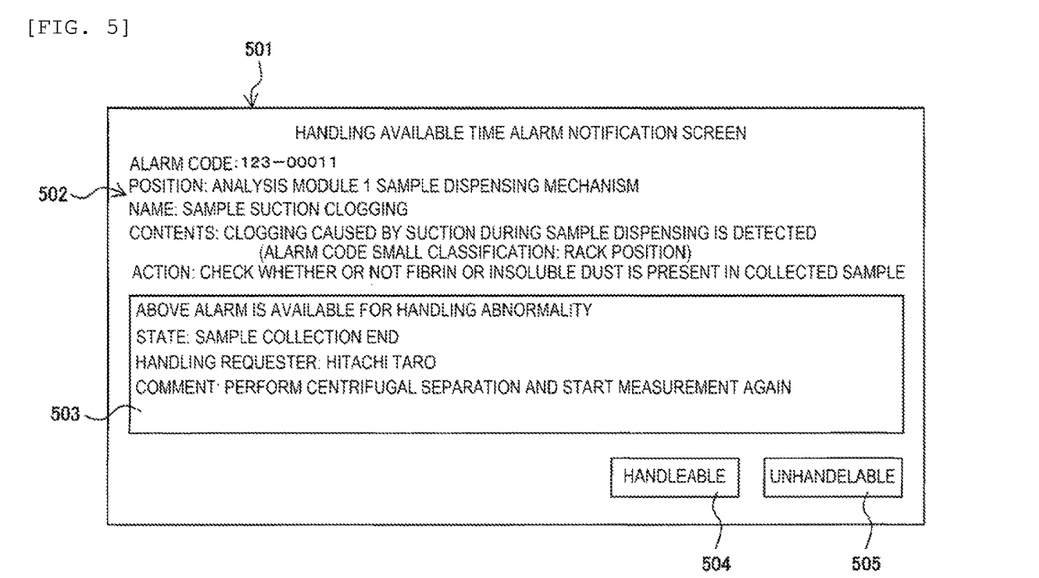
FIG. 5 is a diagram illustrating a handling available alarm notification setting screen.

FIG. 5 is a diagram illustrating a handling available alarm notification setting screen.

The handling available time alarm notification screen 501 illustrated in FIG. 5 is displayed on the display unit 203 of the operating unit PC 111 or the terminal display unit 211 of the remote operation terminal 114a, 114b, or 114c, and is notified and displayed at a timing at which the abnormality target can be handled according to the handling available time notification setting set by the alarm notification setting screen 301 or the abnormality occurrence time alarm notification setting screen 401.

In FIG. 5, for example, the handling available time alarm notification screen 501 includes an alarm content display unit 502 and a handling available time alarm notification content display unit 503.

On the alarm content display unit 502, for example, an alarm code, a position, a name, contents, and an action are displayed as the contents of the alarm for the abnormality.

On the handling available time alarm notification content display unit 503, information regarding the fact that the automatic analyzer is in a state where abnormality can be handled, the user that is requested to handle the abnormality on the abnormality occurrence time alarm notification setting screen 401, the comment from the user, and the like are displayed.

In the handling available time alarm notification content display unit 503, the user to which the alarm is notified presses a handleable button 504 in a case where abnormality can be handled, and presses an unhandleable button 505 in a case where abnormality cannot be handled. As a result, whether or not the system and the user that is requested to handle the abnormality can handle the abnormality, or whether or not it is necessary to request another user to handle the abnormality again can be determined.

Here, the contents of an alarm notification process in the automatic analyzer will be described.

Figure 6:
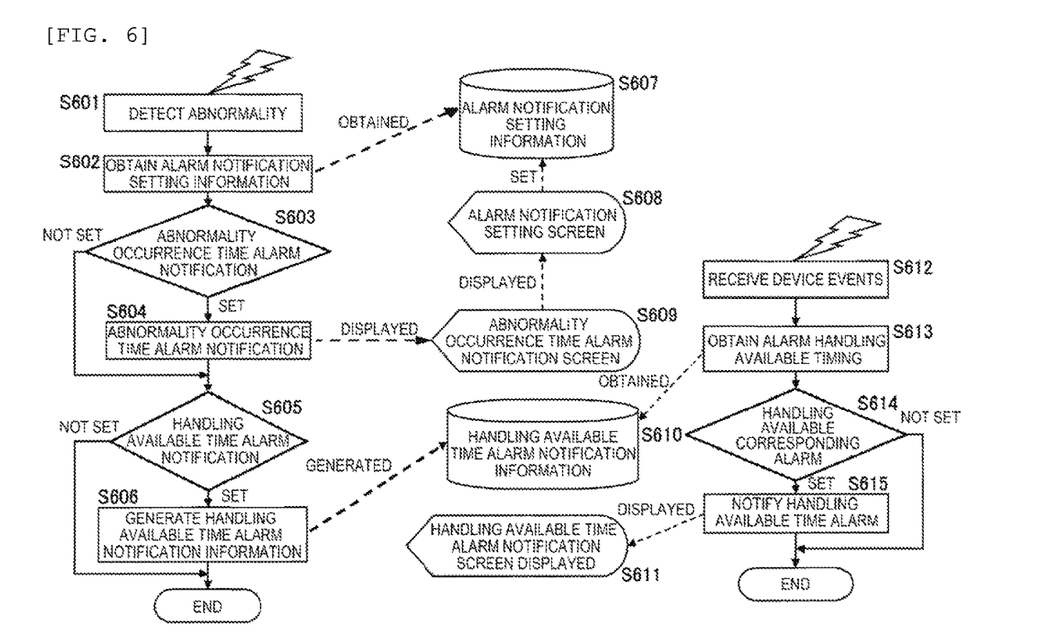
FIG. 6 is a flowchart illustrating the contents of an alarm notification process in the automatic analyzer.

FIG. 6 is a flowchart illustrating the contents of the alarm notification process in the automatic analyzer.

In FIG. 6, in a case where the abnormality detecting unit 208 detects abnormality that occurs in the automatic analyzer 100 (Step S601), the alarm planning unit 206 is preset using alarm information corresponding to the occurred abnormality and the alarm notification setting screen 301 (Step S608), and obtains (Step S602) alarm notification setting information stored (Step S607) in the storage unit 207. Next, the setting of the alarm notification of the abnormality occurrence time is checked (Step S603). In a case where the setting is "Set" (in a case where the notification is set to "Perform"), the alarm is notified of the abnormality occurrence time (Step S604), and the abnormality occurrence time alarm notification setting screen 401 is displayed on the display unit 203 and the terminal display units 211a, 211b, and 211c (Step S609). In a case where the result of the check in Step S603 is "Not Set" (in a case where the notification is set to "Not Perform"), or in a case where the setting of the alarm notification of the handling available time is checked (Step S605) after performing the process of Step S604 and then the setting is "Set" (in a case where the notification is set to "Perform"), alarm notification information of the handling available time is generated and stored in the storage unit 207 (Steps S 606 and S610), and then the process ends. In addition, in a case where the result of the check in Step S605 is "Not Set" ((a case where the notification is set to "Not Perform"), the process also ends.

In addition, in a case where the state managing unit 209 grasps current states of the analyzer, the sample to be used, the reagent, and the like based on information of events occurring in the automatic analyzer 100 (Step S612), the alarm planning unit 206 obtains the alarm notification information of the handling available time from the storage unit 207 (Step S614), and whether or not the alarm that notifies that the device is in a state where the user can handle the abnormality is present is determined based on the current states of the analyzer, the sample to be used, the reagent, and the like and the alarm notification information of the handling available time (Step S614). In a case where the result of the determination in Step S614 is "Present" (in a case where the corresponding alarm is present), the alarm is notified through the handling available time alarm notification screen 501 (Step S615), and the process ends. In addition, in a case where the result of the determination in Step S614 is "Not Present" (in a case where the corresponding alarm is not present), the process ends.

Next, in the automatic analyzer according to the embodiment, the device operation instruction of the abnormality occurrence time, and the timing and the action of the handling available time will be described.

FIG. 7 is a diagram illustrating an example of a correspondence table showing the device operation instruction of the abnormality occurrence time and the timing and the action of the handling available time in the automatic analyzer.

In FIG. 7, a target 701 represents the abnormality target and is classified into the sample, the reagent, the device, and the like. An abnormality 702 represents the contents of abnormality that may occur in the target 701. The device operation instruction 703 of the abnormality occurrence time represents an operation instruction for the device in order to minimize the effects of the abnormality at a timing at which the abnormality occurs or to request the user to handle the abnormality. A timing 704 of the handling available time represents a timing at which the user can handle the abnormality target. In addition, an action 705 of the handling available time represents the contents of the action that is taken by the user at the handling available time. For example, in a case where the abnormality detecting unit 208 detects the contents of any one of the abnormalities 702, the contents of the device operation instruction 703 corresponding to the detected abnormality are displayed on the display unit as the recommended operation of the recommended operation setting unit 304 or the recommended operation of the abnormality occurrence time recommended operation display unit 403. In a case where plural operation instructions are present, the user can select any one of the device operation instructions 703 on the alarm notification setting screen 301 (refer to FIG. 3) or the abnormality occurrence time alarm notification setting screen 401 (refer to FIG. 4). FIG. 4 illustrates the contents corresponding to "Sample Collection" of FIG. 7. In addition, the contents of the timing 704 of the handling available time corresponding to the detected abnormality are displayed on the display unit as the notification timing of the notification timing setting unit 306 or the notification timing of the notification timing setting unit 406. In a case where plural notification timings are present, the user can select any one of the timings 704 of the handling available time on the alarm notification setting screen 301 or the abnormality occurrence time alarm notification setting screen 401. FIG. 4 illustrates the contents corresponding to "sample collection end" in FIG. 7. For the targets and abnormalities other than the sample, the user can also set the recommended operation or the notification timing on the alarm notification setting screen 301 or the abnormality occurrence time alarm notification setting screen 401 based on the correspondence table of FIG. 7.

Regarding a sample 706 that is classified into the target 701, clogging, deficiency, serum information abnormality (such as hemolysis), measurement result abnormality, or the like occurs as the abnormality 702. Examples of the device operation instruction 703 of the abnormality occurrence time includes sample masking of canceling the measurement of the corresponding sample, sample collection of immediately collecting a sample rack on which the corresponding sample is loaded, and sample supply stop of stopping the supply of a new sample. The user determines the operation instruction based on the urgency of the measurement of the sample and the influence of clogging on the device. Examples of the timing 704 of the handling available time include a sample collection end timing at which the sample is collected into the sample housing units and a measurement end timing at which the measurement of all the supplied samples ends. In addition, examples of the action 705 of the handling available time include sample adjustment (for example centrifugal separation) of removing impurity in the sample, replenishment of a sample that is deficient and abnormal, remeasurement of an analysis request item that is abnormal, and measurement of an additional item.

Regarding a reagent 707 that is classified into the target 701, deficiency (reagent deficiency) or measurement result abnormality occurs as the abnormality 702. Regarding the handling of the reagent deficiency, a device that manually registers or disposes the reagent and a device that manually registers or disposes the reagent are present. In the case of the manual device, as the device operation instruction 703 of the abnormality occurrence time, analyzing unit masking of excluding the analyzing unit from the measurement targets and retracting the analyzing unit in order to register or dispose the reagent during the measurement is performed. Examples of the timing 704 of the handling available time include an analyzing unit making end timing at which all the measurement results of the analysis request items of the measurement are output and the analyzing unit is retractable. Examples of the action 705 of the handling available time include an operation of registering or disposing the deficient reagent, releasing the analyzing unit masking, and starting the measurement again. In addition, in the case of the automatic device, examples of the device operation instruction 703 of the abnormality occurrence time include reagent registration. Examples of the timing 704 of the handling available time include a timing at which the automatic reagent distribution of the device ends. In order to distribute the reagent, it is necessary to control mechanisms such as the reagent disk used for the measurement. Therefore, the reagent cannot be immediately distributed during the measurement. In general, the operation of distributing the reagent is scheduled with lower priority than the measurement operation. Therefore, depending on the state of the measurement, a long period of time is required until the distribution. In a case where the abnormality 702 is the measurement result abnormality, reagent masking of excluding the reagent from the subsequent measurement or calibration of correcting a calibration curve is performed as the device operation instruction 703 of the abnormality occurrence time. Examples of the timing 704 of the handling available time include a measurement end timing at which the measurement of all the supplied samples ends. Examples of the action 705 of the handling available time include examination of the reagent and remeasurement after calibration.

Regarding a device 708 that is classified into the target 701, for example, stop level abnormality, sample supply stop level abnormality (the sample supply cannot restart), sample supply stop level abnormality (the sample supply can restart), or negligible level abnormality occurs as the abnormality 702. In a case where the abnormality 702 is the stop level abnormality, the maintenance of the device is performed as the device operation instruction 703 of the abnormality occurrence time. In the case of the stop level abnormality, the device stops, and the abnormality occurrence time is the handling available time. In a case where the abnormality 702 is the sample supply stop level abnormality (the supply cannot restart), a mechanism relating to the sample supply is abnormal, and the sample supply cannot restart. Therefore, the device operation instruction 703 of the abnormality occurrence time is not given. Examples of the timing of the handling available time include a measurement end timing at which the measurement of all the supplied samples ends. Examples of the action 705 of the handling available time include the maintenance of the device. In a case where the abnormality 702 is the sample supply stop level abnormality (the sample supply can restart), some analyzing unit is abnormal, and the sample supply can restart after handling the abnormality. Examples of the device operation instruction 703 of the abnormality occurrence time include analyzing unit masking of excluding the analyzing unit from the measurement targets and retracting the analyzing unit. Examples of the timing 704 of the handling available time include an analyzing unit making end timing at which all the measurement results of the analysis request items of the measurement are output and the analyzing unit is retractable. Examples of the action 705 of the handling available time include an operation of performing the maintenance of the analyzing unit, releasing the analyzing unit masking, and starting the measurement again. In a case where the abnormality 702 is the negligible level abnormality, it is not necessary to immediately handle the abnormality, and the device operation instruction 703 of the abnormality occurrence time is not given. Examples of the timing 704 of the handling available time include a measurement end timing at which the measurement of all the supplied samples ends. Examples of the action 705 of the handling available time include the maintenance of the device.

An abnormality 709 which is already known to the user during the operation is an alarm that is not desired to be notified to the user and is determined and output as abnormality based on a standard abnormality determination theory of the device although the operation of a laboratory or a method of using the device is normal. Therefore, the alarm is set not to be notified of the abnormality occurrence time and of the handling available time.

Regarding the relationship between the device operation instruction of the abnormality occurrence time and the timing and the action of the handling available time, depending on the state of the measurement, several tens of minutes are required from the abnormality occurrence time shown in the sample 706, the reagent 707, and the device 708 to the handling available time, and it is difficult to stop an examination and wait until a timing at which the abnormality can be handled, which leads to a delay of reporting due to deterioration in the examination efficiency and an increase in down time. Accordingly, for example, based on the relationship between the device operation instruction of the abnormality occurrence time and the timing and the action of the handling available time illustrated in FIG. 7, the device can automatically set the alarm notification setting per alarm, the default setting can be optimized, or the user can customize the settings. As a result, whether or not to notify the alarm output from the device can be set according to the operation of a laboratory. In addition, the timing at which the alarm is notified can be set as a timing at which the user can handle the abnormality. Therefore, the device can appropriately notify the alarm that is desired to be notified by the user at a timing at which the abnormality can be handled.

Next, the flow of processes from alarm notification to handling in the automatic analyzer according to the embodiment will be described.

Figure 8:
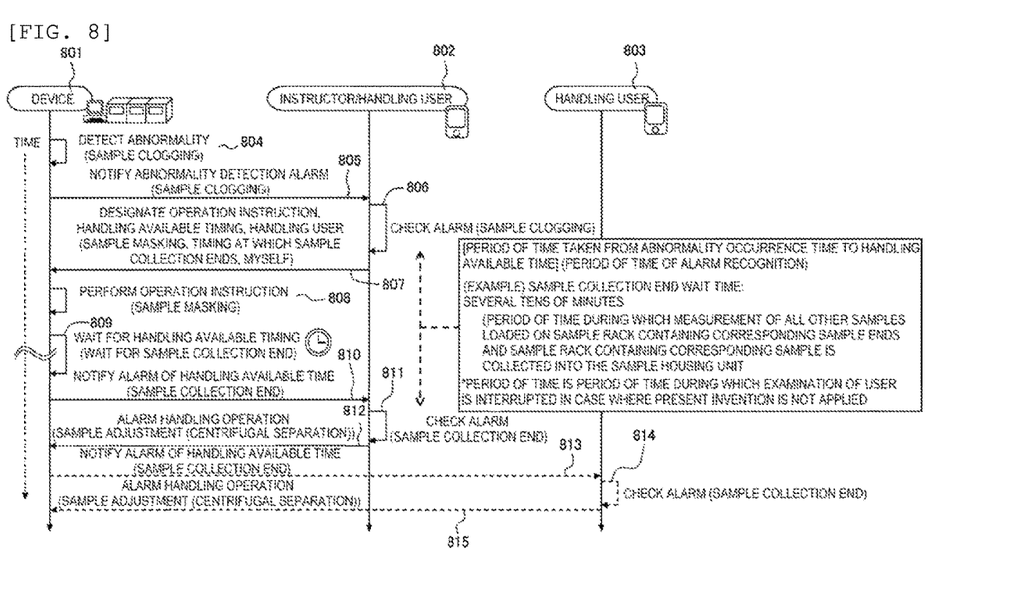
FIG. 8 is a sequence diagram illustrating the flow of processes from alarm notification to handling in the automatic analyzer.

FIG. 8 is a sequence diagram illustrating the flow of processes from alarm notification to handling in the automatic analyzer. In FIG. 8, an example in which the abnormality target is the sample and the content of the abnormality is clogging will be described in detail.

In FIG. 8, a device 801 (an example of the automatic analyzer 100) detects abnormality (sample clogging) using a message 804. The device 801 notifies an alarm (sample clogging) of the detection of abnormality to an instructor/handling user 802 using a message 805. The instructor/handling user 802 checks the alarm (sample clogging) on the abnormality occurrence time alarm notification setting screen 401 using a message (alarm checking) 806. The instructor/handling user 802 (an example of the user 101a, 101b, or 101c) gives an operation instruction (sample masking) through the abnormality occurrence time alarm notification setting screen 401 using a message 807, and designates a handling available timing (at which sample collection ends) and a handling user (itself). The device 801 gives the operation instruction (sample masking) using a message 808. The device 801 waits for a timing (sample collection end) at which the abnormality can be handled using a message 809. The device 801 notifies the alarm (sample collection end) of the handling available time to the instructor/handling user 802 using a message 810. The instructor/handling user 802 checks the alarm (sample collection end) on the handling available time alarm notification screen 501 using a message 811. The instructor/handling user 802 performs an operation of handling the alarm (sample adjustment (centrifugal separation)) on the device 801 using a message 812. In addition, in a case where the instructor/handling user 802 designates a handling user 803 instead of itself using the message 807, the device 801 notifies the alarm (sample collection end) of the handling available time to the handling user 803 using a message 813 instead of the instructor/handling user 802. The handling user 803 checks the alarm (sample collection end) on the handling available time alarm notification screen of FIG. 5 using a message 814. The handling user 803 performs an operation of handling the alarm (sample adjustment (centrifugal separation)) on the device 801 using a message 815.

A period of time taken from the abnormality occurrence time alarm notification (sample clogging) of the message 805 to the alarm handling available time notification (sample collection end) of the message 810 is a period of time taken from the occurrence of sample clogging to the sample collection end, and is a period of time during which the measurement of the other samples loaded on a sample rack containing the sample in which the abnormality (sample clogging) occurs ends and the sample rack containing the sample is collected into the sample housing unit. Regarding the recognition of the instructor/handling user 802, the period of time is a period of time taken from the alarm check 806 relating to the sample clogging to the alarm check 806 relating to the sample collection end. A general sample rack can contain five samples at the same, and at most several tens of minutes are required in consideration of the measurement time required for one sample, the number of samples charged into the device, automatic reexamination, and the like. That is, in a case where the present invention is not applied, only the abnormality occurrence time alarm notification (sample clogging) of the message 805 is performed. Therefore, the state of the device regarding whether or not the sample is collected is checked for a long period of time from the user recognition of the abnormality (sample clogging) to the handling available time (sample collection end). In particular, a sample having high urgency is required to be remeasured urgently, and thus is largely affected. This checking operation has a large load on the user and interrupts an examination.

On the other hand, according to the present invention, the alarm notification is performed in two steps of the abnormality occurrence time and the handling available time. As a result, timely handling and an examination can be focused on, and a reduction in down time and improvement of the examination efficiency can be achieved. In addition, by designating the notification user of the abnormality occurrence time and the handling user of the handling available time, an examination can be performed according to the operation and system of a laboratory.

Next, an alarm notification destination user setting screen in the automatic analyzer according to the embodiment will be described.

Figure 9:
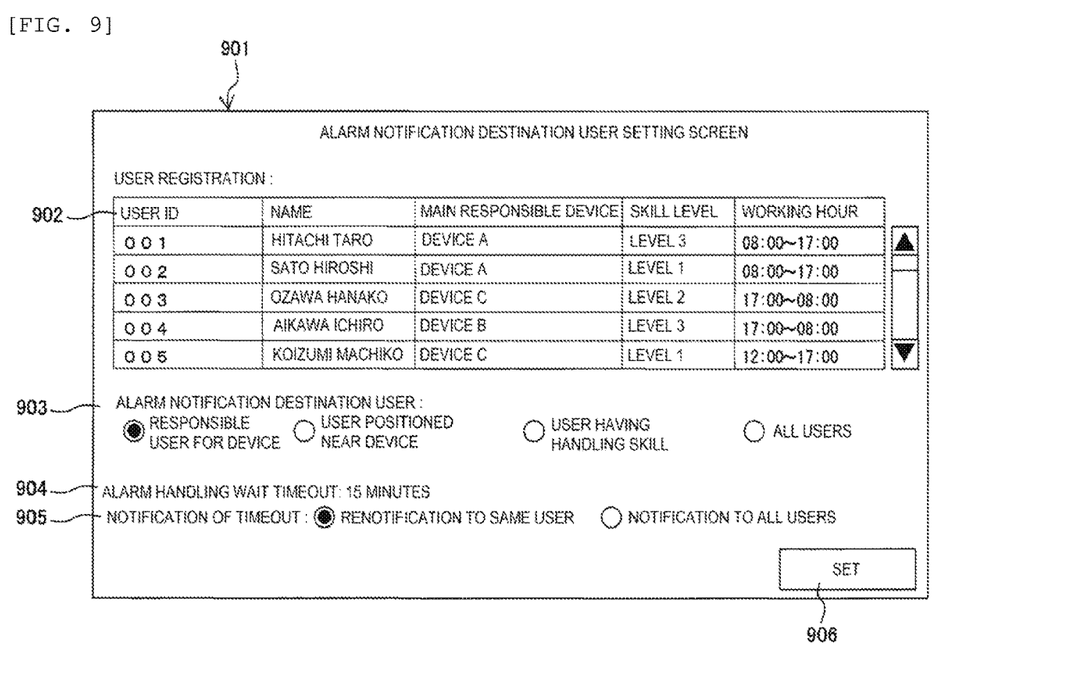
FIG. 9 is a diagram illustrating an alarm notification destination user setting screen.

FIG. 9 is a diagram illustrating the alarm notification destination user setting screen.

The alarm notification destination user setting screen 901 illustrated in FIG. 9 is displayed on the display unit 203 of the operating unit PC 111 or the terminal display unit 211 of the remote operation terminal 114a, 114b, or 114c, and is a screen for registering the user to which the alarm is notified at the abnormality occurrence time or the handling available time.

In FIG. 9, for example, the alarm notification destination user setting screen 901 includes a user registration information input unit 902, an alarm notification destination user setting unit 903, an alarm handling wait timeout time setting unit 904, and a timeout time notification setting unit 905.

The user registration information input unit 902 inputs information of a user as a notification destination of the alarm. As the information of the user, information as a condition for determining the notification destination of the alarm is registered. Specifically, an ID for uniquely identifying the user, a name, a main responsible device, a handling skill level (skill evaluation) of the user, a working hour, and the like are input.

The alarm notification destination user setting unit 903 selectively determines the user to which the alarm is notified when abnormality occurs. Based on the information of the user registration information input unit 902, the alarm is notified to a responsible user for the device, a user having a handling skill, all the users, or a user that is determined to be positioned near a device in which abnormality occurs based on the distance between the device and a remote operation terminal of each of the users.

In the alarm handling wait timeout time setting unit 904, a timeout time until the user as the notification destination handles the abnormality from the alarm notification of the handling available time is set. In a case where the abnormality is not handled even after the set time is elapsed, renotification to the same user or notification to all the users is performed according to the setting of the timeout time notification setting unit 905. That is, whether or not the notified alarm is recognized by the user is checked (recognition checking) or whether or not an operation for improving the abnormality corresponding to the alarm is performed is checked, for example, by operating the handleable button 504 or the unhandleable button 505 of the handling available time alarm notification screen 501. Next, in a case where the check is not performed until a predetermined time is elapsed from the alarm notification, the notifying unit is caused to notify the alarm again (renotification to the same user or notification to all the users).

The set button 906 is a button for storing the setting contents input by the alarm notification destination user setting screen 901 in the storage unit 207.

Next, the flow of the alarm notification process of the automatic analyzer according to the embodiment by plural users will be described.

Figure 10:
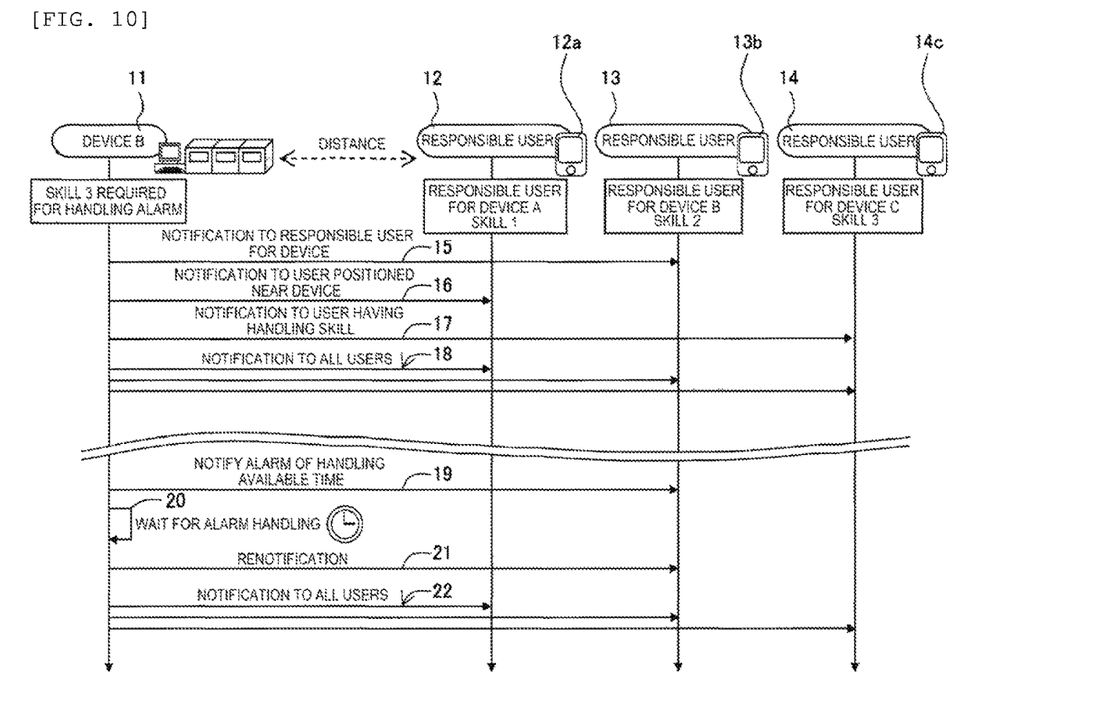
FIG. 10 is a sequence diagram illustrating the flow of the alarm notification process of the automatic analyzer by plural users.

FIG. 10 is a sequence diagram illustrating the flow of the alarm notification process of the automatic analyzer by plural users. In FIG. 10, the description will be made by using a device B11 as an example of the automatic analyzer 100 is and using users 12, 13, and 14 and remote operation terminals 12a, 13b, and 14c as examples of the users 101a, 101b, and 101c and the remote operation terminals 114a, 114b, and 114c, respectively.

In FIG. 10, when abnormality occurs in the device B11 (the example of the automatic analyzer 100), the alarm is notified according to the setting of the alarm notification destination user setting unit 903 of the alarm notification destination user setting screen 901.

That is, in the alarm notification destination user setting unit 903, in a case where "the responsible user for the device" is set, the alarm is notified to the responsible user 13 (the remote operation terminal 13b of the user 13 in charge) for the device (device B) using a message 15. In addition, in a case where "the user positioned near the device" is set, the alarm is notified to the responsible user 12 (the remote operation terminal 12a of the responsible user 12) positioned nearest to the device using a message 16. In addition, in a case where "the skill having a handling skill" is set, the alarm is notified to the responsible user 14 (the remote operation terminal 14c of the responsible user 14) having a skill required for handling using a message 17. In addition, in a case where "all the users" is set, the alarm is notified to all the responsible users 12, 13, and 14 using a message 18.

Next, the alarm of the handling available time is notified according to the settings of the alarm handling wait timeout time setting unit 904 and the timeout time notification setting unit 905 of the alarm notification destination user setting screen 901.

That is, the alarm of the handling available time is notified from the device B11 to the responsible user 13 using a message 19. The device B11 waits for the report of the responsible user 13 for handling for the time set by the alarm handling wait timeout time setting unit 904 using a message 20. In a case where the set time is elapsed, the device B11 performs renotification according to the setting of the timeout time notification setting unit 905. In a case where "renotification" is set, the alarm is renotified to the responsible user 13 to which the alarm is initially notified using a message 21. In addition, in a case where "notification to all the users" is set, the alarm is notified to all the responsible users 12, 13, and 14 using a message 22.

For example, based on the information relating to the attributes of the user or he relationship between the device and the user that is registered in advance, the device notifies the alarm to an appropriate user, and in a case where the notified user cannot handle the alarm, the device notify the alarm to another user. This way, the device has a recovery function. As a result, even in a case where an examination is operated by plural users and plural devices, an appropriate user can handle the alarm timely, and a reduction in the down time of a laboratory as a whole and improvement of the examination efficiency can be achieved.

In addition, in a case where plural users or plural devices are operated in the same laboratory, it is expected that the setting information of the alarm notification setting screen 301 or the alarm notification destination user setting screen 901 will be operated with the same setting in all the devices. Therefore, it is preferable that a function of sharing or copying information through a network or a storage medium is provided so as to share the setting information between the devices or with higher-level systems.

The effects of the embodiment having the above-described configuration will be described.

In general, the operation of an automatic analyzer varies depending on individual laboratories in many cases. Accordingly, in a case where the operation contents regarding the determination or reporting of abnormality do not match with conditions set in an automatic analyzer, the contents of an alarm generated by the automatic analyzer do not match with the operation in a laboratory, which may lead to deterioration in examination efficiency or a delay of examination result reporting.

On the other hand, according to the embodiment, there is provided an automatic analyzer that performs analysis using a sample and a reagent, the automatic analyzer including: a device state managing unit that manages a device state of the automatic analyzer; an abnormality detecting unit that detects abnormality of the automatic analyzer based on information of the device state managed by the device state managing unit and a predetermined reference; an alarm planning unit that plans at least two alarms including an abnormality occurrence alarm and an handling available alarm regarding each of abnormality items detected by the abnormality detecting unit, the abnormality occurrence alarm being planned for notification to a user in a case where the abnormality occurs, and the handling available alarm being planned for notification to the user in a case where the automatic analyzer is in a device state where the automatic analyzer is available for handling the abnormality; and a notifying unit that notifies the alarms planned by the alarm planning unit. Therefore, deterioration in examination efficiency or a delay of examination result reporting can be prevented.

The present invention is not limited to the embodiment and includes various modification examples. For example, the embodiment has been described in detail in order to easily describe the present invention, and the present invention is not necessarily to include all the configurations described above.

REFERENCE SIGNS LIST

11: device B
12, 13, 14: responsible user
12a, 13b, 14c: remote operation terminal
100: automatic analyzer
101a, 101b, 101c: user
102: sample container
102a: tag
103: sample rack
104: sample loading unit
105: transportation line
106a, 106b, 106c: analyzing unit
107: reagent container
108a, 108b, 108c: reagent disk
109: sample housing unit
110: communication device
112: higher-level host system
113: wireless device
114a, 114b, 114c: remote operation terminal
120a, 120b, 120c: reaction disk
121a, 121b, 121c: sample dispensing mechanism
122a, 122b, 122c: reagent dispensing mechanism
123a, 123b, 123c: photometric mechanism
200: configuration
201: communication
202: input unit
203: display unit
204: notifying unit (alarm notifying unit)
205: communication unit
206: alarm planning unit
207: storage unit
208: abnormality detecting unit
209: state managing unit
210: remote operation terminal
211: terminal display unit 211a, 211b, 211c: terminal display unit
212: terminal communication unit
213: terminal input unit
214: terminal position detecting unit
301: alarm notification setting screen
302: alarm content display unit
303: notification setting unit
304: recommended operation setting unit
305: notification setting unit
306: notification timing setting unit
307: set button
308: abnormality occurrence time notification setting unit
309: handling available time notification setting unit
401: abnormality occurrence time alarm notification setting screen
402: alarm content display unit
403: abnormality occurrence time recommended operation display unit
404: perform button
405: notification setting unit
406: notification timing setting unit
407: notification destination setting unit
408: comment input unit
409: set button
411: handling available time notification setting unit
501: handling available time alarm notification screen
502: alarm content display unit
503: handling available time alarm notification content display unit
504: handleable button
505: unhandleable button
801: device
802: instructor/handling user
803: handling user
901: alarm notification destination user setting screen
902: user registration information input unit
903: alarm notification destination user setting unit
904: timeout time setting unit
905: timeout time notification setting unit
906: set button

The invention claimed is:

1. An automatic analyzer that performs analysis using a sample and a reagent, the automatic analyzer comprising:
a photometric mechanism to perform analysis of the sample and the reagent;
an operating unit computer including an input unit, a display unit, and a storage unit, wherein the operating unit computer is configured to perform the steps of:
determining a current state of the automatic analyzer based on information received from the automatic analyzer;
detecting whether the current state of the automatic analyzer indicates an abnormality type of the automatic analyzer based on a comparison of the current state with a predetermined reference state for the automatic analyzer;
determining a first alarm time and a second alarm time at which to provide alarm signals for the abnormality type based on a comparison of the indicated abnormality type with prestored information, wherein
the first alarm time is selected to notify a user of an occurrence time of the abnormality type, the second alarm time is selected to notify a user of a preferred time at which a process of improving the abnormality type is executable, and the first alarm time is a period of time before the second alarm time;
providing the alarm signals at the first and second alarm times; and
determining the user to be responsible to respond to the alarm signals provided for the automatic analyzer based on user skill evaluation information, user working hour information, an operation required for improving the abnormality type, and an abnormality occurrence time.

2. The automatic analyzer according to claim 1, wherein the operating unit computer is configured to perform the further step comprising:
presetting whether or not the alarm signals are provided at the first and second alarm times for each of a plurality of abnormality types.

3. The automatic analyzer according to claim 1, wherein the operating unit computer is configured to perform the further step comprising:
presetting a determination criterion for determining that the automatic analyzer is in a device state where the automatic analyzer is available for handling the abnormality type.

4. The automatic analyzer according to claim 1, wherein the display unit displays a recommended operation to be performed by the user to handle the indicated abnormality type and a second alarm time at which the automatic analyzer is in a device state for the user to handle the abnormality type.

5. The automatic analyzer according to claim 1, wherein the operating unit computer is configured to perform the further steps comprising:
providing for selectively setting the second alarm time from among a plurality of predetermined time candidates, and
causing the display unit to display the plurality of predetermined time candidates at the first alarm time.

6. The automatic analyzer according to claim 1, wherein the operating unit computer is configured to perform the further steps comprising:
determining whether or not an alarm signal is recognized by the user or determining whether or not an operation for improving the abnormality type corresponding to the alarm signal is performed, and
repeating the alarm signal after a predetermined time lapse based on the determination of whether or not the alarm signal is recognized or whether or not the operation for improving the abnormality type is performed.

7. The automatic analyzer according to claim 1, wherein the alarm signals are provided at a center of a display device or by generating a warning sound.

8. The automatic analyzer according to claim 1, further comprising:
a remote operation terminal associated with the user, said remote operation terminal configured to communicate with the automatic analyzer, wherein
the alarm signals are transmitted to the remote operation terminal.

9. The automatic analyzer according to claim 8, wherein the remote operation terminal includes a terminal position detecting unit configured to detect a current position of the remote operation terminal, and
the alarm signals are transmitted to the remote operation terminal based on the current position of the remote operation terminal.

* * * * *